(12) United States Patent
Cauwet-Martin et al.

(10) Patent No.: US 6,423,305 B1
(45) Date of Patent: Jul. 23, 2002

(54) COSMETIC COMPOSITION COMPRISING AT LEAST AN AMIDOETHERCARBOXYLIC ACID SURFACTANT AND AT LEAST A CATIONIC POLYMER/ANIONIC POLYMER COMBINATION

(75) Inventors: Danièle Cauwet-Martin; Nathalie Garnier, both of Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/380,088

(22) PCT Filed: Dec. 10, 1998

(86) PCT No.: PCT/FR98/02687

§ 371 (c)(1),
(2), (4) Date: Oct. 26, 1999

(87) PCT Pub. No.: WO99/33444

PCT Pub. Date: Jul. 8, 1999

(30) Foreign Application Priority Data

Dec. 29, 1997 (FR) .............................. 97 16629

(51) Int. Cl.[7] .......................... A61K 7/06; A61K 7/00; A61K 7/08; A61K 7/075
(52) U.S. Cl. ..................... 424/70.19; 424/47; 424/70.1; 424/70.11; 510/119
(58) Field of Search .......................... 424/401, 70.19, 424/70.1, 47, 70.11; 510/119

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,272,780 A | 2/1942 | Dittmar |
| 2,375,853 A | 5/1945 | Kirby et al. |
| 2,388,614 A | 11/1945 | Kirby et al. |
| 2,454,547 A | 11/1948 | Book et al. |
| 2,528,378 A | 10/1950 | Manheimer |
| 2,723,248 A | 11/1955 | Wright |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,874,870 A | 4/1975 | Green et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,128,631 A | 12/1978 | Lundmark et al. |
| 4,131,576 A | 12/1978 | Iovine et al. |
| 4,185,087 A | 1/1980 | Morlino |
| 4,693,935 A | 9/1987 | Mazurek |
| 4,728,571 A | 3/1988 | Clemens et al. |
| 4,803,221 A | 2/1989 | Bair |
| 4,972,037 A | 11/1990 | Garbe et al. |
| 5,661,118 A * | 8/1997 | Cauwet et al. |
| 5,783,535 A * | 7/1998 | Isobe et al. |
| 6,022,836 A * | 2/2000 | Dubief et al. |

FOREIGN PATENT DOCUMENTS

| | | |
|---|---|---|
| DE | 23 30 956 | 1/1974 |
| EP | 0 095 238 | 11/1983 |
| EP | 0 102 118 | 3/1984 |
| EP | 0 122 324 | 10/1984 |
| EP | 0 337 354 | 10/1989 |
| EP | 0 412 704 | 2/1991 |
| EP | 0 412 707 | 2/1991 |
| EP | 0 440 542 | 8/1991 |
| EP | 0 582 152 | 2/1994 |
| EP | 0 690 044 | 1/1996 |
| EP | 0 699 435 | 3/1996 |
| EP | 0 733 355 | 9/1996 |
| EP | 0 761 205 | 3/1997 |
| FR | 1 222 944 | 6/1960 |
| FR | 1 564 110 | 4/1969 |
| FR | 1 580 545 | 9/1969 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 198 719 | 4/1974 |
| FR | 2 265 781 | 10/1975 |
| FR | 2 265 782 | 10/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 350 384 | 12/1977 |
| FR | 2 357 241 | 2/1978 |
| FR | 2 383 660 | 10/1978 |
| FR | 2 393 573 | 1/1979 |

(List continued on next page.)

OTHER PUBLICATIONS

Amihud Krmaer, "Revised Tables for Determining Significance of Difference", Food Technology, vol. 17, No. 12, Dec. 1963, pp. 124–125.

(List continued on next page.)

*Primary Examiner*—Thurman K. Page
*Assistant Examiner*—Brian K. Seidleck
(74) *Attorney, Agent, or Firm*—Finnegan, Henderson, Farabow, Garrett & Dunner, L.L.P.

(57) ABSTRACT

The present invention relates to a cosmetic composition for the treatment of keratinous substances, in particular the hair, comprising, in a cosmetically acceptable medium, at least one amido ether carboxylic acid surfactant and at least one combination of at least one anionic polymer and of at least one cationic polymer. The compositions according to the invention are used in particular as rinse-out products, especially for washing and retaining the hairstyle or shaping the hairstyle.

41 Claims, No Drawings

FOREIGN PATENT DOCUMENTS

| | | |
|---|---|---|
| FR | 2 413 907 | 8/1979 |
| FR | 2 439 798 | 5/1980 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| GB | 0 839 805 | 6/1960 |
| WO | 93/23009 | 11/1993 |
| WO | 93/23446 | 11/1993 |
| WO | 95/00578 | 1/1995 |

OTHER PUBLICATIONS

M.R. Porter, "Non–Ionics", Handbook of Surfactants, Blacie (Glasgow and London), 1991, pp. 117–178.
English language Derwent Abstract of DE 2 330 956.
English language Derwent Abstract of FR 1 564 110.
English language Derwent Abstract of FR 1 580 545.
English language Derwent Abstract of FR 1 583 363.
English language Derwent Abstract of FR 2 077 143.
English language Derwent Abstract of FR 2 080 759.
English language Derwent Abstract of FR 2 162 055.
English language Derwent Abstract of FR 2 190 406.
English language Derwent Abstract of FR 2 265 781.
English language Derwent Abstract of FR 2 265 782.
English language Derwent Abstract of FR 2 270 846.
English language Derwent Abstract of FR 2 280 361.
English language Derwent Abstract of FR 2 316 271.
English language Derwent Abstract of FR 2 320 330.
English language Derwent Abstract of FR 2 336 434.
English language Derwent Abstract of FR 2 350 384.
English language Derwent Abstract of FR 2 357 241.
English language Derwent Abstract of FR 2 383 660.
English language Derwent Abstract of FR 2 393 573.
English language Derwent Abstract of FR 2 413 907.
English language Derwent Abstract of FR 2 439 798.
English language Derwent Abstract of FR 2 470 596.
English language Derwent Abstract of FR 2 505 348.
English language Derwent Abstract of FR 2 519 863.
English language Derwent Abstract of FR 2 542 997.
English language Derwent Abstract of FR 2 598 611.
English language Derwent Abstract of JP 09 165597.
English language Derwent Abstract of EP 0 440 542.

* cited by examiner

COSMETIC COMPOSITION COMPRISING AT LEAST AN AMIDOETHERCARBOXYLIC ACID SURFACTANT AND AT LEAST A CATIONIC POLYMER/ANIONIC POLYMER COMBINATION

This application is a 371 of PCT/FR98/02687, filed Dec. 10, 1998.

The present invention relates to a cosmetic or dermatological composition comprising, in a cosmetically or dermatologically acceptable medium, at least one amido ether carboxylic acid surfactant and at least one combination of at least one noncrosslinked anionic polymer and of at least one cationic polymer.

Compositions, in particular leave-in hair compositions, comprising an anionic polymer and a cationic polymer are known in the state of the art. These compositions exhibit good styling properties. However, when these polymer combinations are used in rinse-out compositions, such as shampoos, the styling properties of these compositions are not satisfactory. Thus, an alkyl ether carboxylate surfactant has already been combined, in Patent FR 2,383,660, with a cationic polymer and an anionic polymer. On one hand, the styling properties are not satisfactory and, on the other hand, the foaming power of such a composition is insufficient.

The target is to obtain cosmetic compositions which are capable of contributing, to the hair, properties of styling, of body, of shaping and of hold while having good cosmetic properties, such as softness, feel or disentangling, as well as a sufficient foaming power for them to be used as a shampoo composition.

The Applicant Company has discovered, surprisingly, that, by combining at least one alkylamido ether carboxylic acid surfactant or its salts with at least one combination of an anionic polymer and of a cationic polymer, the styling, body, shaping and hold properties of the hair were substantially superior to those obtained with the surfactants of the prior art used in combination with the anionic polymer and the cationic polymer.

The composition according to the invention is therefore essentially characterized in that it comprises, in a cosmetically or dermatologically acceptable medium, at least one amido ether carboxylic acid surfactant or its salts and at least one combination of at least one noncrosslinked anionic polymer and of at least one cationic polymer.

Another subject-matter of the invention is the use of the composition described above for the styling or the shaping of the hair.

The amido ether carboxylic acid surfactant generally exhibits the following formula (I):

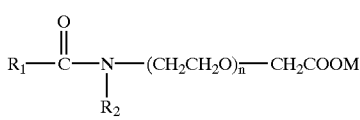

(I)

in which $R_1$ denotes a linear or branched, alkyl or alkenyl radical having from 5 to 23 carbon atoms or a phenyl radical substituted by an alkyl radical having from 6 to 10 carbon atoms. $R_1$ preferably denotes an alkyl radical having from 8 to 18 carbon atoms and more particularly from 10 to 16 carbon atoms. $R_2$ denotes a hydrogen atom, an alkyl radical having from 1 to 3 carbon atoms, a —$(CH_2CH_2O)_n$$CH_2COOM$ radical or a —$(CH_2CH_2O)_m$ radical and preferably a hydrogen atom; n and m, which are identical or different, represent a number between 1 and 20, preferably between 1 and 10 and more particularly between 1 and 5. M denotes a hydrogen atom, an alkali metal (for example $Na^+$ or $K^+$), $NH_4^+$ or ammoniums comprising a residue chosen from basic amino acids, such as lysine, arginine, sarcosine, ornithine or citrulline, or else from aminoalcohols, such as monoethanolamine, diethanolamine, triethanolamine, glucamine, N-methylglucamine or 3-amino-1,2-propanediol.

These amido ether carboxylic acid compounds are described in particular in Patent Applications EP-A-699,435 and EP-A-102,118.

A particularly preferred amido ether carboxylic acid surfactant is the sodium salt of formula:

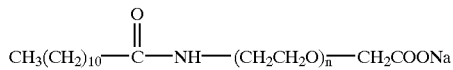

in which n has a mean value of 3.

Such a compound is, for example, sold under the name Akypofoam 30 BV by the company Chem Y.

According to the invention, use may be made of any noncrosslinked anionic polymer or of any cationic polymer known per se. These polymers can be used in dissolved form or in the form of dispersions of solid polymer particles.

The noncrosslinked anionic polymers generally used are polymers comprising groups derived from carboxylic, sulphonic or phosphoric acid and have a weight-average molecular weight of between approximately 500 and 5,000,000.

1) The carboxyl groups are contributed by unsaturated mono- or dicarboxylic acid monomers such as those corresponding to the formula:

(II)

in which n is an integer from 0 to 10, A denotes a methylene group, optionally bonded to the carbon atom of the unsaturated group or to the neighbouring methylene group when n is greater than 1 via a heteroatom, such as oxygen or sulphur, $R_5$ denotes a hydrogen atom or a phenyl or benzyl group, $R_3$ denotes a hydrogen atom or a lower alkyl or carboxyl group, and $R_4$ denotes a hydrogen atom, a lower alkyl group or a —$CH_2$—COOH, phenyl or benzyl group. In the abovementioned formula, a lower alkyl radical preferably denotes a group having 1 to 4 carbon atoms and in particular methyl and ethyl.

The preferred anionic polymers comprising carboxyl groups according to the invention are:

A) homo- or copolymers of acrylic or methacrylic acid or their salts and in particular the products sold under the names Versicol E or K by the company Allied Colloid and Ultrahold by the company BASF, the copolymers of acrylic acid and of acrylamide sold in the form of their sodium salt under the names Reten 421, 423 or 425 by the Company Hercules or the sodium salts of polyhydroxycarboxylic acids.

B) copolymers of acrylic or methacrylic acid with a monoethylenic monomer, such as ethylene, styrene, vinyl esters or esters of acrylic or methacrylic acid. These copolymers can be grafted onto a polyalkylene glycol, such as polyethylene glycol. Such polymers are disclosed in particular in French Patent 1,222,944 and German Application 2,330,956. Mention may in particular be made of the copolymers comprising, in their chain, an optionally N-alkylated and/or -hydroxyalkylated acrylamide unit, such as disclosed in particular in Luxembourgian Patent Applications 75370 and 75371 or provided under the name Quadramer by the Company American Cyanamid. Mention may also be made of copolymers of acrylic acid and of $C_1$–$C_4$ alkyl methacrylate and terpolymers of vinylpyrrolidone, of (meth)acrylic acid and of $C_1$–$C_{20}$ alkyl (meth)acrylate, for example lauryl (meth)acrylate (such as that sold by the company ISP under the name Acrylidone LM), tert-butyl (meth)acrylate (Luviflex VBM 70, sold by BASF) or methyl (meth)acrylate (Stepanhold Extra, sold by Stepan), and methacrylic acid/ethyl acrylate/tert-butyl acrylate terpolymers, such as the product sold under the name Luvimer 100 P by the company BASF.

C) copolymers derived from crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbon chain, such as those comprising at least 5 carbon atoms, it optionally being possible for these polymers to be grafted, or alternatively a vinyl, allyl or methallyl ester of an α- or β-cyclic carboxylic acid. Such polymers are disclosed, inter alia, in French Patents 1,222,944, 1,580,545, 2,265,782, 2,265,781, 1,564,110 and 2,439,798. Commercial products coming within this class are the Resins 28-29-30, 26-13-14 and 28-13-10 sold by the company National Starch.

D) copolymers derived from $C_4$–$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated; such polymers are disclosed in particular in U.S. Pat. Nos. 2,047,398, 2,723,248 and 2,102,113 and Patent GB 839,805 and in particular those sold under the names Gantrez AN or ES, or Avantage CP by the company ISP.

copolymers comprising (i) one or more maleic, citraconic or itaconic anhydrides and (ii) one or more monomers chosen from allyl or methallyl esters, optionally comprising one or more acrylamide, methacrylamide or α-olefin groups, acrylic or methacrylic esters, acrylic acid, methacrylic acid or vinylpyrrolidone in their chain, the anhydride functional groups of these copolymers optionally being monoesterified or monoamidated. These polymers are, for example, disclosed in French Patents 2,350,384 and 2,357,241 of the Applicant Company.

E) polyacrylamides comprising carboxylate groups.

The polymers comprising sulpho groups are polymers comprising vinylsulphonic, styrenesulphonic, naphthalenesulphonic or acrylamidoalkylsulphonic units.

These polymers can in particular be chosen from:

salts of polyvinylsulphonic acid having a weight-average molecular weight of between approximately 1000 and 100,000, as well as copolymers with an unsaturated comonomer, such as acrylic or methacrylic acids and their esters as well as acrylamide or its derivatives, vinyl ethers and vinylpyrrolidone.

salts of polystyrenesulphonic acid, the sodium salts having a weight-average molecular weight of approximately 500,000 and of approximately 100,000 sold respectively under the names Flexan 500 and Flexan 130 by National Starch. These compounds are disclosed in Patent FR 2,198,719.

salts of polyacrylamidosulphonic acids, such as those mentioned in U.S. Pat. No. 4,128,631 and more particularly the polyacrylamidoethylpropanesulphonic acid sold under the name Cosmedia Polymer HSP 1180 by Henkel.

According to the invention, the anionic polymers are preferably chosen from acrylic acid copolymers, such as the acrylic acid/ethyl acrylate/N-tert-butylacrylamide terpolymers sold in particular under the name Ultrahold Strong by the company BASF, copolymers derived from crotonic acid, such as the vinyl acetate/vinyl tert-butyl-benzoate/crotonic acid terpolymers and the crotonic acid/vinyl acetate/vinyl neododecanoate terpolymers sold in particular under the name Resin 28-29-30 by the company National Starch, polymers derived from maleic, fumaric or itaconic acids or anhydrides with vinyl esters, vinyl ethers, vinyl halides, phenylvinyl derivatives, or acrylic acid and its esters, such as the monoesterified methyl vinyl ether/maleic anhydride copolymers sold, for example, under the name Gantrez by the company ISP, copolymers of methacrylic acid and of methyl methacrylate sold under the name Eudragit L by the company Rohm Pharma, methacrylic acid/methyl methacrylate/$C_1$–$C_4$ alkyl acrylate/acrylic acid or $C_1$–$C_4$ hydroxyalkyl methacrylate copolymers sold in the form of dispersions under the name Amerhold DR 25 by the company Amerchol or under the name Acudyne 255 by the company Röhm & Haas, copolymers of methacrylic acid and of ethyl acrylate sold under the name Luvimer MAEX or MAE by the company BASF and vinyl acetate/crotonic acid copolymers, vinyl acetate/crotonic acid copolymers grafted by polyethylene glycol sold under the name Aristoflex A by the company BASF, or acrylic or methacrylic acid homopolymers sold, for example, under the name Versicol E 5.

The most particularly preferred noncrosslinked anionic polymers are chosen from the monoesterified methyl vinyl ether/maleic anhydride copolymers sold under the name Gantrez ES 425 by the company ISP, the acrylic acid/ethyl acrylate/N-tert-butylacrylamide terpolymers sold under the name Ultrahold Strong by the company BASF, the copolymers of methacrylic acid and of methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer MAEX or MAE by the company BASF, the vinylpyrrolidone/acrylic acid/lauryl methacrylate terpolymers sold under the name Acrylidone LM by the company ISP and the acrylic or methacrylic acid homopolymers sold, for example, under the name Versicol E 5.

According to the invention, use may also be made of anionic polymers in the latex or pseudolatex form, that is to say in the form of a dispersion of insoluble polymer particles.

According to the invention, use may also be made of anionic polymers of grafted silicone type comprising a polysiloxane portion and a portion composed of a non-silicone organic chain, one of the two portions constituting the main chain of the polymer and the other being grafted onto the said main chain. These polymers are, for example, disclosed in Patent Applications EP-A-0,412,704, EP-A-0, 412,707, EP-A-0,640,105 and WO 95/00578, EP-A-0,582, 152 and WO 93/23009 and U.S. Pat. Nos. 4,693,935, 4,728,571 and 4,972,037.

Such polymers are, for example, the copolymers which can be obtained by radical polymerization from the mixture of monomers composed of:

a) 50 to 90% by weight of tert-butyl acrylate;
b) 1 to 40% by weight of acrylic acid;
c) 5 to 40% by weight of silicone macromer of formula:

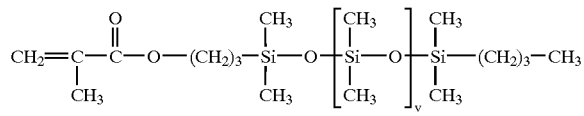

with v being a number ranging from 5 to 700; the percentages by weight being calculated with respect to the total weight of the monomers.

One family of silicone polymers with a polysiloxane skeleton grafted with non-silicone organic monomers which is particularly well suited to the implementation of the present invention is composed of the silicone polymers comprising, in their structure, the following unit of the formula (III):

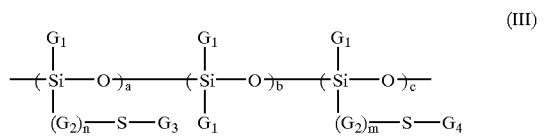

in which the $G_1$ radicals, which are identical or different, represent hydrogen or a $C_1$–$C_{10}$ alkyl radical or a phenyl radical; the $G_2$ radicals, which are identical or different, represent a $C_1$–$C_{10}$ alkylene group; $G_3$ represents a polymeric residue resulting from the (homo)polymerization of at least one anionic monomer possessing ethylenic unsaturation; $G_4$ represents a polymeric residue resulting from the (homo)polymerization of at least one hydrophobic monomer possessing ethylenic unsaturation; m and n are equal to 0 or 1; a is an integer ranging from 0 to 50; b is an integer which can be between 10 and 350 and c is an integer ranging from 0 to 50; with the proviso that one of the parameters a and c is other than 0.

The unit of formula (III) above preferably exhibits at least one, and more preferably still all, of the following characteristics:

the $G_1$ radicals denote a $C_1$–$C_{10}$ alkyl radical, preferably the methyl radical;

n is nonzero and the $G_2$ radicals represent a divalent $C_1$–$C_3$ radical, preferably a propylene radical;

$G_3$ represents a polymeric radical resulting from the (homo)polymerization of at least one monomer of the carboxylic acid possessing ethylenic unsaturation type, preferably acrylic acid and/or methacrylic acid;

$G_4$ represents a polymeric radical resulting from the (homo)polymerization of at least one monomer of the $C_1$–$C_{10}$ alkyl (meth)acrylate type, preferably isobutyl or methyl (meth)acrylate.

The unit of formula (III) above can also preferably exhibit all of the following characteristics:

the $G_1$ radicals denote a $C_1$–$C_{10}$ alkyl radical, preferably the methyl radical;

n is nonzero and the $G_2$ radicals represent a divalent $C_1$–$C_3$ radical, preferably a propylene radical;

$G_3$ represents a polymeric radical resulting from the (homo)polymerization of at least one monomer of the carboxylic acid possessing ethylenic unsaturation type, preferably acrylic acid and/or methacrylic acid;

c is equal to zero.

Examples of grafted silicone polymers are in particular polydimethylsiloxanes (PDMS) on which are grafted, via a connecting link of thiopropylene type, mixed polymer units of the poly((meth)acrylic acid) type and of the poly(alkyl (meth)acrylate) type, such as poly(isobutyl (meth)acrylate). Use is particularly made of the grafted silicone polymers of formula (III) with a polymethyl/methylsiloxane structure comprising poly(methacrylic acid)-3-thiopropyl groups and poly(methyl methacrylate)-3-thiopropyl groups and the grafted silicone polymers of formula (III) with a polymethyl/methylsiloxane structure comprising poly(acrylic acid)-3-thiopropyl groups.

The cationic polymers which can be used in accordance with the present invention can be chosen from all those already known per se, in particular those disclosed in Patent Application EP-A-0,337,354 and in French Patent Applications FR-A-2,270,846, 2,383,660, 2,598,611, 2,470,596 and 2,519,863.

More generally still, within the meaning of the present invention, the expression "cationic polymer" denotes any polymer comprising cationic groups or groups which can be ionized to cationic groups.

The preferred cationic polymers are chosen from those which comprise units comprising primary, secondary, tertiary and/or quaternary amine groups which can either form part of the main polymer chain or be carried by a side substituent directly connected to the latter.

The cationic polymers used generally have a number-average molecular mass of between 500 and $5 \times 10^6$ approximately and preferably of between $10^3$ and $3 \times 10^6$ approximately.

Mention may more particularly be made, among the cationic polymers, of the polymers of the polyamine, polyaminoamide and poly(quaternary ammonium) type. These are known products.

One family of cationic polymers is that of the silicone cationic polymers. Mention may be made, among these polymers, of: (a) silicone polymers corresponding to the following formula (IV):

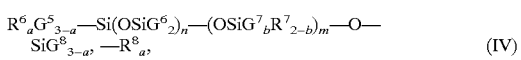

in which:

$G^5$, $G^6$, $G^7$ and $G^8$, which are identical or different, denote a hydrogen atom or a phenyl, OH, $C_1$–$C_{18}$ alkyl, for example methyl, $C_2$–$C_{18}$ alkenyl or $C_1$–$C_{18}$ alkoxy group, a and a', which are identical or different, denote the number 0 or an integer from 1 to 3, in particular 0, b denotes 0 or 1 and in particular 1, m and n are numbers such that the sum (n+m) can vary in particular from 1 to 2000 and especially from 50 to 150, it being possible for n to denote a number from 0 to 1999 and in particular from 49 to 149 and it being possible for m to denote a number from 1 to 2000 and in particular from 1 to 10, $R^6$, $R^7$ and $R^8$, which are identical or different, denote a monovalent radical of the formula $-C_qH_{2q}O_sR^9_tL$, in which q is a number from 1 to 8, s and t, which are identical or different, are equal to 0 or to 1, $R^9$ denotes an optionally hydroxylated alkylene group and L is an optionally quaternized amino group chosen from the groups:

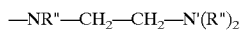

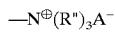

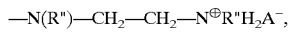

in which R″ can denote hydrogen, phenyl, benzyl or a saturated monovalent hydrocarbon-comprising radical, for example an alkyl radical having from 1 to 20 carbon atoms, and A⁻ represents a halide ion, such as, for example, fluoride, chloride, bromide or iodide.

Products corresponding to this definition are, for example, the polysiloxanes named "amodimethicone" in the CTFA dictionary and corresponding to the following formula (V):

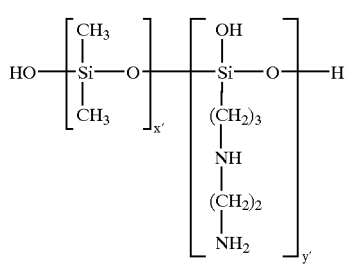

in which x' and y' are integers depending on the molecular weight, generally such that the said molecular weight is between 5000 and 20,000 approximately.

A product corresponding to the formula (IV) is the polymer named "trimethylsilylamodimethicone" in the CTFA dictionary, corresponding to the formula:

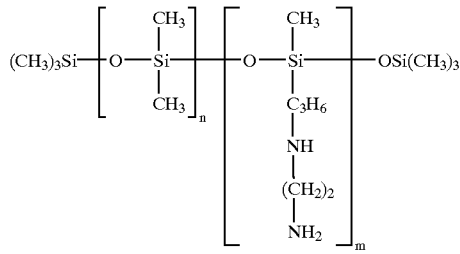

in which n and m have the meanings given above (cf. formula IV).

A commercial product corresponding to this definition is a mixture (90/10 by weight) of a polydimethylsiloxane comprising aminoethylaminoisobutyl groups and of a polydimethylsiloxane sold under the name Q2-8220 by the company Dow Corning.

Such polymers are disclosed, for example, in Patent Application EP-A-95,238.

Other polymers corresponding to the formula (IV) are the silicone polymers corresponding to the following formula (VI):

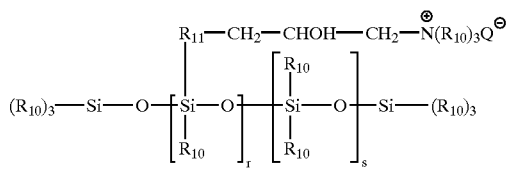

in which:

$R_{10}$ represents a monovalent hydrocarbon-comprising radical having from 1 to 18 carbon atoms and in particular a $C_1$–$C_{18}$ alkyl or $C_2$–$C_{18}$ alkenyl radical, for example a methyl radical;

$R_{11}$ represents a divalent hydrocarbon-comprising radical, in particular a $C_1$–$C_{18}$ alkylene radical or a divalent $C_1$–$C_{18}$ alkyleneoxy radical, for example a $C_1$–$C_8$ radical;

$Q^-$ is a halide ion, in particular a chloride ion; r represents a mean statistical value of 2 to 20 and in particular of 2 to 8;

s represents a mean statistical value of 20 to 200 and in particular of 20 to 50.

Such polymers are disclosed more particularly in U.S. Pat. No. 4,185,087. (b) the compounds of formula: NH—[(CH$_2$)$_3$—Si[OSi(CH$_3$)$_3$]]$_3$ corresponding to the CTFA name "aminobispropyldimethicone".

A polymer coming within this class is the polymer sold by the Company Union Carbide under the name "Ucar Silicone ALE 56".

When these silicone polymers are employed, a particularly advantageous embodiment is their joint use with cationic and/or nonionic surfactants. Use may be made, for example, of the products sold under the name "Emulsion Cationique DC 929" [Cationic Emulsion DC 929] by the Company Dow Corning, which comprises, in addition to amodimethicone, a cationic surfactant comprising a mixture of products corresponding to the formula (VII):

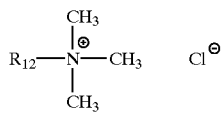

in which $R_{12}$ denotes alkenyl and/or alkyl radicals having from 14 to 22 carbon atoms which are derived from tallow fatty acids, in combination with a nonionic surfactant of formula:

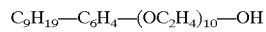

known under the name "Nonoxynol 10".

Another commercial product which can be used according to the invention is the product sold under the name "Dow Corning Q2 7224" by the Company Dow Corning comprising, in combination, the trimethylsilylamodimethicone of formula (IV), a nonionic surfactant of formula: $C_8H_{17}$—$C_6H_4$—$(OCH_2CH_2)_n$—OH, where n=40, also known as octoxynol-40, another nonionic surfactant of formula: $C_{12}H_{25}$—$(OCH_2$—$CH_2)_n$—OH, where n=6, also known as isolaureth-6, and glycol.

The polymers of the polyamine, polyaminoamide or poly(quaternary ammonium) type which can be used in accordance with the present invention which can be mentioned in particular are those disclosed in French Patents No. 2,505, 348 or 2,542,997. Mention may be made, among these polymers, of:

(1) optionally quaternized vinylpyrrolidone/ dialkylaminoalkyl acrylate or methacrylate copolymers, such as the products sold under the name "Gafquat®" by the Company ISP, such as, for example, Gafquat 734, 755 or HS100, or else the product named "Copolymer 937". These polymers are disclosed in detail in French Patents 2,077,143 and 2,393,573.

(2) cellulose ether derivatives comprising quaternary ammonium groups disclosed in French Patent 1,492,597 and in particular the polymers sold under the names "JR" (JR 400, JR 125, JR 30M) or "LR" (LR 400, LR 30M) by the Company Union Carbide Corporation. These polymers are also defined in the CTFA dictionary as quaternary ammoniums of hydroxyethylcellulose having reacted with an epoxide substituted by a trimethylammonium group.

(3) cationic cellulose derivatives, such as the copolymers of cellulose or the cellulose derivatives grafted with a water-soluble quaternary ammonium monomer and disclosed in particular in U.S. Pat. No. 4,131,576, such as hydroxyalkyl celluloses, for example hydroxymethyl, hydroxyethyl or hydroxypropyl celluloses, grafted in particular with a methacryloylethyltrimethylammonium, methacrylamidopropyltrimethylammonium or dimethyldiallylammonium salt.

The marketed products corresponding to this definition are more particularly the products sold under the name "Celquat L 200" and "Celquat H 100" by the Company National Starch.

(4) the cationic polysaccharides disclosed more particularly in U.S. Pat. Nos. 3,589,578 and 4,031,307 and more particularly the product sold under the name "Jaguar C.13 S" by the Company Meyhall.

(5) polymers composed of piperazinyl units and of divalent, straight- or branched-chain alkylene or hydroxyalkylene radicals, optionally interrupted by oxygen, sulphur or nitrogen atoms or by aromatic or heterocyclic rings, as well as the oxidation and/or quaternization products of these polymers. Such polymers are disclosed in particular in French Patents 2,162,025 and 2,280,361.

(6) water-soluble polyaminoamides prepared in particular by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide; these polyaminoamides can be alkylated or, if they comprise one or more tertiary amine functional groups, quaternized. Such polymers are disclosed in particular in French Patents 2,252,840 and 2,368,508.

(7) polyaminoamide derivatives resulting from the condensation of polyalkylenepolyamines with polycarboxylic acids, followed by an alkylation by bifunctional agents. Mention may be made, for example, of adipic acid/dialkylaminohydroxyalkyl/dialkylenetriamine polymers in which the alkyl radical comprises from 1 to 4 carbon atoms and preferably denotes methyl, ethyl or propyl. Such polymers are disclosed in particular in French Patent 1,583,363.

Mention may more particularly be made, among these derivatives, of the adipic acid/dimethylaminohydroxypropyl/diethylenetriamine polymers sold under the name "Cartaretine F, F4 or F8" by the company Sandoz.

(8) polymers obtained by reaction of a polyalkylenepolyamine comprising two primary amine groups and at least one secondary amine group with a dicarboxylic acid chosen from diglycolic acid and saturated aliphatic dicarboxylic acids having from 3 to 8 carbon atoms, the molar ratio of polyalkylenepolyamine to dicarboxylic acid being between 0.8:1 and 1.4:1; the polyaminoamide resulting therefrom being brought to react with epichlorohydrin in a molar ratio of epichlorohydrin in relation to the secondary amine group of the polyaminoamide of between 0.5:1 and 1.8:1. Such polymers are disclosed in particular in U.S. Pat. Nos. 3,227,615 and 2,961,347.

Polymers of this type are in particular sold under the name "Hercosett 57" by the company Hercules Inc. or else under the name of "PD 170" or "Delsette 101" by the company Hercules in the case of the adipic acid/epoxypropyl/diethylenetriamine copolymer.

(9) cyclopolymers of methyldiallylamine or of diallyldimethylammonium, such as the homopolymers or the copolymers comprising, as main constituent of the chain, units corresponding to the formulae (VIII) or (VIII'):

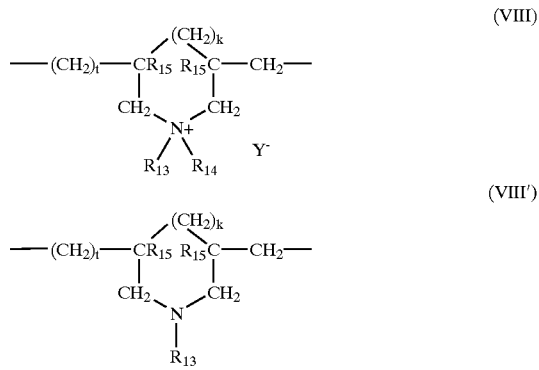

in which formulae k and t are equal to 0 or 1, the sum k+t being equal to 1; $R_{15}$ denotes a hydrogen atom or a methyl radical; $R_{13}$ and $R_{14}$, independently of one another, denote an alkyl group having from 1 to 22 carbon atoms, a hydroxyalkyl group in which the alkyl group preferably has 1 to 5 carbon atoms or a lower amidoalkyl group or $R_{13}$ and $R_{14}$ can denote, jointly with the nitrogen atom to which they are attached, heterocyclic groups, such as piperidinyl or morpholinyl; $Y^-$ is an anion, such as bromide, chloride, acetate, borate, citrate, tartrate, bisulphate, bisulphite, sulphate or phosphate. These polymers are disclosed in particular in French Patent 2,080,759 and in its Certificate of Addition 2,190,406.

Mention may be made, for example, of the homopolymer of diallyldimethylammonium chloride sold under the name "Merquat 100" by the company Merck and of the copolymers of diallyldimethylammonium chloride and of acrylamide sold under the name "Merquat 550".

(10) the quaternary diammonium polymer comprising repeat units corresponding to the formula (IX):

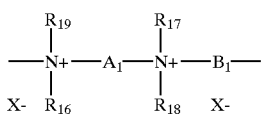

in which formula (IX):

$R_{16}$, $R_{17}$, $R_{18}$ and $R_{19}$, which are identical or different, represent aliphatic, alicyclic or arylaliphatic radicals comprising from 1 to 20 carbon atoms or lower hydroxyalkyl aliphatic radicals or $R_{16}$, $R_{17}$, $R_{18}$ and $R_{19}$, together or separately, form, with the nitrogen atoms to which they are attached, heterocycles optionally comprising a second heteroatom other than nitrogen or else $R_{16}$, $R_{17}$, $R_{18}$ and $R_{19}$ represent a linear or branched $C_1$–$C_6$ alkyl radical substituted by a nitrile, ester, acyl, amide or —CO—O—$R_{20}$—D or —CO—NH—$R_{20}$—D group, where $R_{20}$ is an alkylene and D a quaternary ammonium group;

$A_1$ and $B_1$ represent polymethylene groups comprising from 2 to 20 carbon atoms which can be linear or branched, saturated or unsaturated, and which can contain, bonded to or inserted into the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{16}$ and $R_{18}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a $(CH_2)_n$—CO—D—OC—$(CH_2)_n$— group in which D denotes:

a) a glycol residue of formula: —O—Z—O—, where Z denotes a linear or branched hydrocarbon-comprising radical or a group corresponding to one of the following formulae:

—(CH$_2$—CH$_2$—O)$_x$—CH$_2$—CH$_2$—

[CH$_2$—CH(CH$_3$)—O]$_y$CH$_2$—CH(CH$_3$)— where x and y denote an integer from 1 to 4, representing a defined and unique degree of polymerization, or any number from 1 to 4 representing a mean degree of polymerization;

b) a bissecondary diamine residue, such as a piperazine derivative;

c) a bisprimary diamine residue of formula: —NH—Y—NH—, where Y denotes a linear or branched hydrocarbon-comprising radical or else the divalent radical

—CH$_2$—CH$_2$—S—S—CH$_2$—CH$_2$—;

d) a ureylene group of formula: —NH—CO—NH—.

Preferably, $X^-$ is an anion, such as chloride or bromide.

These polymers have a number-average molecular mass generally of between 1000 and 100,000.

Polymers of this type are disclosed in particular in French Patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

11) polymers of poly(quaternary ammonium)s composed of units of formula (X):

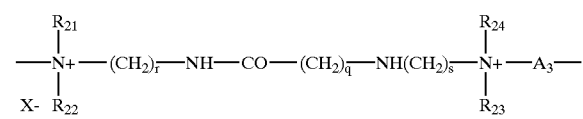

in which formula:

$R_{21}$, $R_{22}$, $R_{23}$ and $R_{24}$, which are identical or different, represent a hydrogen atom or a methyl, ethyl, propyl, β-hydroxyethyl, β-hydroxypropyl or —CH$_2$CH$_2$(OCH$_2$CH$_2$)$_p$OH radical, where p is equal to 0 or to an integer of between 1 and 6, with the proviso that $R_{21}$, $R_{22}$, $R_{23}$ and $R_{24}$ do not simultaneously represent a hydrogen atom, r and s, which are identical or different, are integers of between 1 and 6, q is equal to 0 or to an integer of between 1 and 34, X denotes a halogen atom, $A_3$ denotes a radical from a dihalide or preferably represents —CH$_2$—CH$_2$—O—CH$_2$—CH$_2$—.

Such compounds are disclosed in particular in Patent Application EP-A-122,324.

Mention may be made among these, for example, of the products "Mirapol® A 15", "Mirapol® AD1", "Mirapol® AZ1" and "Mirapol® 175", sold by the company Miranol.

(12) homopolymers or copolymers derived from acrylic or methacrylic acids and comprising units:

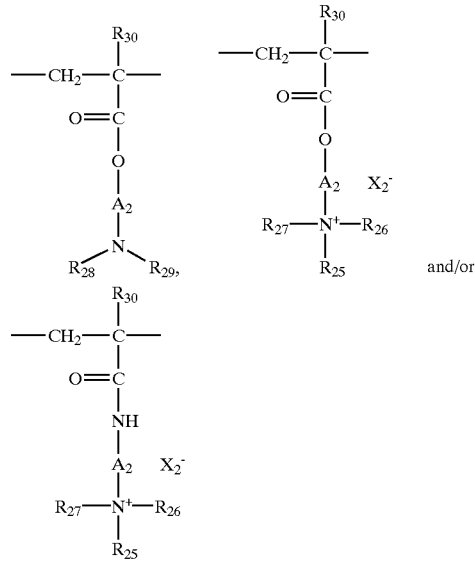

and/or in which the $R_{30}$ groups independently denote H or $CH_3$, the $A_2$ groups independently denote a linear or branched alkyl group of 1 to 6 carbon atoms or a hydroxyalkyl group of 1 to 4 carbon atoms, the $R_{25}$, $R_{26}$ and $R_{27}$ groups, which are identical or different, independently denote an alkyl group of 1 to 18 carbon atoms or a benzyl radical, the $R_{28}$ and $R_{29}$ groups represent a hydrogen atom or an alkyl group of 1 to 6 carbon atoms, $X_2^-$ denotes an anion, for example methyl sulphate or halide, such as chloride or bromide.

The comonomer or comonomers which can be used in the preparation of the corresponding copolymers belong to the family of acrylamides, methacrylamides, diacetone acrylamides, acrylamides and methacrylamides substituted at the nitrogen by lower alkyls, alkyl esters of acrylic or methacrylic acid, vinylpyrrolidone or vinyl esters.

(13) quaternary polymers of vinylpyrrolidone and of vinylimidazole, such as, for example, the products sold under the names Luviquat® FC 905, FC 550 and FC 370 by the company BASF.

(14) polyamines, such as Polyquart H sold by Henkel, referenced under the name "Polyethylene Glycol (15) Tallow Polyamine" in the CTFA dictionary.

(15) crosslinked polymers of methacryloyloxyethyltrimethylammonium chloride, such as the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by a crosslinking by a compound possessing olefinic unsaturation, in particular methylenebisacrylamide. Use may more particularly be made of a crosslinked acrylamide/methacryloyloxyethyltrimethylammonium chloride (20/80 by weight) copolymer in the form of a dispersion comprising 50% by weight of the said copolymer in mineral oil. This dispersion is sold under the name of "Salcare SC 92" by the Company Allied Colloids. Use may also be made of a crosslinked homopolymer of methacryloyloxyethyltrimethylammonium chloride comprising approximately 50% by weight of the homopolymer in mineral oil. This dispersion is sold under the name of "Salcare® SC 95" by the Company Allied Colloids.

Other cationic polymers which can be used in the context of the invention are polyalkyleneimines, in particular polyethyleneimines, polymers comprising vinylpyridine or vinylpyridinium units, condensates of polyamines and of epichlorohydrin, quaternary polyureylenes and chitin derivatives.

Preference is given, among all the cationic polymers which can be used in the context of the present invention, to the use of cyclopolymers, in particular copolymers of dimethyldiallylammonium chloride and of acrylamide having a molecular weight of greater than 500,000, sold under the names "Merquat 550" and "Merquat® S" by the Company Merck, cationic polysaccharides and more particularly the polymer sold under the name "Jaguar® C13S" by the Company Meyhall, and polyaminoamides of the family (6) which are described above.

According to the invention, it is also possible to use cationic polymers in the latex or pseudolatex form, that is to say in the form of a dispersion of insoluble polymer particles.

According to the invention, the anionic polymer or polymers can represent from 0.01% to 20% by weight, preferably from 0.05% to 15% by weight and more preferably still from 0.1% to 7% by weight of the total weight of the final composition.

According to the invention, the cationic polymer or polymers can represent from 0.01% to 20% by weight, preferably from 0.1% to 15% by weight and more preferably still from 0.5% to 5% by weight of the total weight of the final composition.

According to the invention, the amido ether carboxylic acid surfactant or surfactants can represent from 0.1% to 30% by weight, preferably from 0.5% to 20% by weight and more preferably still from 1% to 15% by weight of the total weight of the final composition.

The cationic charge of the cationic polymer(s)/anionic charge of the anionic polymer(s) ratio, expressed in meq/g, is generally between 0.25 and 5, preferably between 0.5 and 2 and more preferably still between 0.75 and 1.25.

The cationic charge is the quaternary, tertiary, secondary or primary amine atom number per gram of polymer.

The cosmetically or dermatologically acceptable medium is preferably composed of water or a mixture of water and of cosmetically or dermatologically acceptable solvents, such as monoalcohols, polyalcohols, glycol ethers or fatty acid esters, which can be used alone or as a mixture.

Mention may more particularly be made of lower alcohols, such as ethanol or isopropanol, polyalcohols, such as diethylene glycol, or glycol ethers, such as glycol or diethylene glycol alkyl ethers.

The composition of the invention can also comprise at least one additive chosen from sequestering agents, softeners, foam-modifying agents, colorants, pearlescent agents, moisturizing agents, antidandruff or antiseborrhoeic agents, suspending agents, ceramides, pseudoceramides, fatty acids with linear or branched $C_{16}$–$C_{40}$ chains, hydroxy acids, electrolytes, thickeners, fatty acid esters, esters of fatty acids and of glycerol, silicones, surfactants, fragrances, preservatives, sunscreen agents, proteins, vitamins, nonionic polymers, vegetable, animal, mineral or synthetic oils and any other additive conventionally used in the cosmetics field.

These additives are present in the composition according to the invention in proportions which can range from 0 to 40% by weight with respect to the total weight of the composition. The precise amount of each additive depends on its nature and is readily determined by a person skilled in the art.

Of course, a person skilled in the art will take care to choose the possible compound or compounds to be added to the composition according to the invention so that the advantageous properties intrinsically attached to the composition in accordance with the invention are not, or not substantially, detrimentally affected by the envisaged addition.

The compositions according to the invention can be provided in the form of a gel, milk, cream, more or less thickened lotion, or foam.

The compositions according to the invention are generally used as products in particular for washing, caring for, conditioning or retaining the hair-style or shaping keratinous substances, such as the hair.

The compositions of the invention can more particularly be provided in the form of a shampoo or conditioner to be rinsed out or left in or of permanent-wave, hair-straightening, dyeing or bleaching compositions or alternatively in the form of compositions to be applied before or after a dyeing, a bleaching, a permanent wave or a hair straightening process or alternatively between the two stages of a permanent wave or of a hair straightening. The compositions are preferably washing compositions.

The compositions according to the invention, when they are provided in particular in the form of washing compositions, such as shampoos, comprise a washing base, generally an aqueous washing base.

The surfactant or surfactants forming the washing base can be chosen without distinction, alone or as mixtures, from anionic, amphoteric, nonionic, zwitterionic and cationic surfactants.

The minimum amount of washing base is that just sufficient to confer a satisfactory foaming and/or detergent power on the final composition.

Thus, according to the invention, the washing base can represent from 4% to 30% by weight, preferably from 10% to 25% by weight and more preferably still from 12% to 20% by weight of the total weight of the final composition.

The surfactants which are suitable for the implementation of the present invention are in particular the following:

(i) Anionic Surfactant(s)

Their nature does not assume a really critical character within the context of the present invention.

Thus, mention may in particular be made, by way of example of anionic surfactants which can be used, alone or as mixtures, in the context of the present invention, of (non-limiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylaryl polyether sulphates or monoglyceride sulphates; alkyl sulphonates, alkyl phosphates, alkylamido sulphonates, alkylaryl sulphonates, α-olefin sulphonates or paraffin sulphonates; alkyl sulphosuccinates, alkyl ether sulphosuccinates or alkylamide sulphosuccinates; alkylsulphosuccinamates; alkyl sulphoacetates; alkyl ether phosphates; acylsarcosinates; acylisethionates and N-acyltaurates, the alkyl or acyl radical of all these different compounds preferably comprising from 8 to 24 carbon atoms and the aryl radical preferably denoting a phenyl or benzyl group. Mention may also be made, among the anionic surfactants which can be used further, of the salts of fatty acids, such as the salts of oleic, ricinoleic, palmitic and stearic acids, or the acids of coconut oil or of hydrogenated coconut oil; or acyllactylates in which the acyl radical comprises 8 to 20 carbon atoms. Use may also be made of weakly anionic surfactants, such as alkyl D-galactoside uronic acids and their salts, as well as of polyoxyalkylenated ($C_6$–$C_{24}$)alkyl ether carboxylic acids, polyoxyalkylenated ($C_6$–$C_{24}$)alkylaryl ether carboxylic acids and their salts, in particular those comprising from 2 to 50 ethylene oxide groups, and their mixtures.

Use is preferably made according to the invention, among the anionic surfactants, of alkyl sulphate and alkyl ether sulphate salts and their mixtures.

(ii) Nonionic Surfactant(s)

The nonionic surface-active agents themselves are also compounds which are well known per se (in this respect see in particular the "Handbook of Surfactants" by M. R. Porter, published by Blackie & Son (Glasgow and London), 1991, pp. 116–178) and, in the context of the present invention, their nature does not assume any critical character. They can thus be chosen in particular from (non-limiting list) alcohols, alphadiols, alkylphenols or fatty acids which are polyethoxylated, polypropoxylated or polyglycerolated having a fatty chain comprising, for example, 8 to 18 carbon atoms, it being possible for the number of ethylene oxide or propylene oxide groups to range in particular from 2 to 50 and it being possible for the number of glycerol groups to range in particular from 2 to 30. Mention may also be made of the copolymers of ethylene and propylene oxide or of the condensates of ethylene and propylene oxide with fatty alcohols; the polyethoxylated fatty amides preferably having from 2 to 30 mol of ethylene oxide, the polyglycerolated fatty amides on average comprising 1 to 5 glycerol groups and in particular 1.5 to 4; the polyethoxylated fatty amines preferably having 2 to 30 mol of ethylene oxide;

the oxyethylenated fatty acid esters of sorbitan having from 2 to 30 mol of ethylene oxide; the fatty acid esters of sucrose, the fatty acid esters of polyethylene glycol, the alkyl polyglycosides, the N-alkylglucamine derivatives, or the amine oxides, such as the oxides of ($C_{10}$–$C_{14}$) alkylamines or the N-acylaminopropylmorpholine oxides. It will be noted that alkyl polyglycosides constitute nonionic surfactants which enter particularly well into the scope of the present invention.

(iii) Amphoteric or Zwitterionic Surfactant(s)

The amphoteric or zwitterionic surface-active agents, the nature of which does not assume any critical character in the context of the present invention, may be in particular (non-limiting list) derivatives of aliphatic secondary or tertiary amines in which the aliphatic radical is a linear or branched chain comprising 8 to 18 carbon atoms and comprising at least one water-solubilizing anionic group (for example carboxylate, sulphonate, sulphate, phosphate or phosphonate); mention may also be made of ($C_8$–$C_{20}$)alkyl betaines, sulphobetaines, ($C_8$–$C_{20}$)alkyl amido($C_1$–$C_6$)alkyl betaines or ($C_8$–$C_{20}$)alkyl amido($C_1$–$C_6$)alkyl sulphobetaines.

Mention may be made, among the amine derivatives, of the products sold under the name Miranol, as disclosed in U.S. Pat. Nos. 2,528,378 and 2,781,354 and classified in the CTFA dictionary, 3rd edition, 1982, under the names Amphocarboxyglycinates and Amphocarboxypropionates with respective structures:

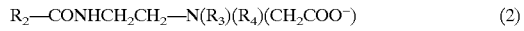
$$R_2\text{—CONHCH}_2\text{CH}_2\text{—N}(R_3)(R_4)(\text{CH}_2\text{COO}^-) \qquad (2)$$

in which:
R$_2$ denotes an alkyl radical of an acid R$_2$—COOH present in hydrolysed coconut oil or a heptyl, nonyl or undecyl radical, R$_3$ denotes a β-hydroxyethyl group and R$_4$ denotes a carboxymethyl group; and

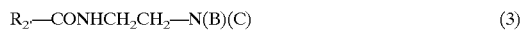
$$R_2\text{—CONHCH}_2\text{CH}_2\text{—N(B)(C)} \qquad (3)$$

in which:
B represents —CH$_2$CH$_2$OX', C represents —(CH$_2$)$_z$—Y', with z=1 or 2,
X' denotes the —CH$_2$CH$_2$—COOH group or a hydrogen atom,
Y' denotes —COOH or the —CH$_2$—CHOH—SO$_3$H radical,
R$_2$, denotes an alkyl radical of an acid R$_9$—COOH present in hydrolysed linseed oil or coconut oil, an alkyl radical, in particular a $C_7$, $C_9$, $C_{11}$ or $C_{13}$ radical, a $C_{17}$ alkyl radical and its iso form, or an unsaturated $C_{17}$ radical.

By way of example, mention may be made of the cocoamphocarboxyglycinate sold under the trade name Miranol $C_2M$ concentrate by the Company Miranol.

(iv) Cationic Surfactants

Mention may in particular be made, among the cationic surfactants, the nature of which does not assume any critical character in the context of the present invention, of (non-limiting list): the salts of optionally polyoxyalkylenated primary, secondary or tertiary fatty amines; quaternary ammonium salts, such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

When the composition according to the invention is packaged in aerosol form for the purpose of obtaining an aerosol foam, it comprises at least one propellant which can be chosen from volatile hydrocarbons, such as n-butane, propane, isobutane or pentane, a chlorinated and/or fluorinated hydrocarbon and their mixtures. Use may also be made, as propellant, of carbon dioxide gas, nitrous oxide, dimethyl ether, nitrogen, compressed air and their mixtures.

Another subject-matter of the invention is a process for the cosmetic treatment of keratinous substances, such as the hair, which consists in applying, to the latter, a composition as defined above and in then optionally rinsing with water.

The invention will now be more fully illustrated using the following examples, which should not be regarded as limiting it to the embodiments described. In what follows, AM means Active Material.

EXAMPLE 1

Two shampoos were prepared with the following composition:

Shampooing is carried out by applying approximately 1 g of the composition A to locks of 2.5 g of prewetted slightly bleached hair. The shampoo is lathered, the hair is left standing for 10 minutes and then it is copiously rinsed with water. The locks of hair are dried at 60° C. for 30 min. The comparative composition B is used according to the same procedure as above.

A panel of experts evaluated the hardening of the dried hair.

The object of the test used is the classification, by a jury, of each series of 2 samples as an increasing or decreasing function of the effectiveness of the hardening. The 2 locks of the same series are presented simultaneously to the judge. He or she is asked to classify them from the most hardened to the least hardened. The statistical analysis of the results is carried out using the tables of A. Kramer (Food Technology, 17(12), 124–125, 1963).

Results

| Testers | 1 | 2 | 3 | 4 | 5 | 6 | 7 | 8 | 9 | 10 | Σ of the grades |
|---|---|---|---|---|---|---|---|---|---|---|---|
| Lock A | 1 | 1 | 1 | 1 | 1 | 1 | 1 | 1 | 1 | 1 | 10 |
| Lock B | 2 | 2 | 2 | 2 | 2 | 2 | 2 | 2 | 2 | 2 | 20 |

Conclusion

The locks treated with the composition A according to the invention comprising the alkylamido ether carboxylic surfactant are significantly harder (at the 5% level) than those treated with the composition comprising the surfactant of the prior art.

|  | A (invention) | B |
|---|---|---|
| Sodium salt of formula: 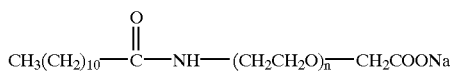 in which n has a mean value of 3 (Akypofoam 30 BV from Chem Y) | 12 g AM | — |
| Sodium salt of formula: $CH_3(CH_2)_{11}$—O—$(CH_2CH_2O)_n$—$CH_2COONa$ in which n has a mean value of 4.5 (Akyposoft NV45 from Chem Y) | — | 12 g AM |
| Grafted silicone polymer of formula (III) with the structure: polymethyl/methylsiloxane comprising poly(methacrylic acid)-3-thio-propyl groups, as a 12% by weight aqueous solution | 1 g AM | 1 g AM |
| Polycondensate of adipic acid and of diethylenetriamine crosslinked with epichlorohydrin as a 20% by weight aqueous solution | 2.22 g AM | 2.22 g AM |
| NaOH q.s. | pH 8 | pH 8 |
| NaCl | 2 g | 2 g |
| Fragrance, preservative | q.s. | q.s. |
| Demineralized water q.s. for | 100 g | 100 g |

EXAMPLE 2

A shampoo is prepared with the following composition:

| | A (invention) | B |
|---|---|---|
| Sodium salt of formula: $CH_3(CH_2)_{10}-\overset{O}{\overset{\|}{C}}-NH-(CH_2CH_2O)_{\overline{n}}-CH_2COONa$ in which n has a mean value of 3 (Akypofoam 30 BV from Chem Y) | 12 g AM | — |
| Sodium salt of formula: $CH_3(CH_2)_{11}-O-(CH_2CH_2O)_n-CH_2COONa$ in which n has a mean value of 4.5 (Akyposoft NV45 from Chem Y) | — | 12 g AM |
| Poly(acrylic acid) as a 25% aqueous solution (Versicol E 5 from Allied Colloid) | 1 g AM | 1 g AM |
| Polycondensate of adipic acid and of diethylenetriamine crosslinked with epichlorohydrin as a 20% by weight aqueous solution | 3.03 g AM | 3.03 g AM |
| NaOH q.s. | pH 8 | pH 8 |
| NaCl | 2 g | 2 g |
| Fragrance, preservative | q.s. | q.s. |
| Demineralized water q.s. for | 100 g | 100 g |

Shampooing is carried out by applying approximately 1 g of the composition A to locks of 2.5 g of prewetted slightly bleached hair. The shampoo is lathered, the hair is left standing for 10 minutes and then it is copiously rinsed with water. The locks of hair are dried at 60° C. for 30 min. The comparative composition P is used according to the same procedure as above.

A panel of experts evaluated the hardening of the dried hair.

The object of the test used is the classification, by a jury, of each series of 2 samples as an increasing or decreasing function of the effectiveness of the hardening. The 2 locks of the same series are presented simultaneously to the judge. He or she is asked to classify them from the most hardened to the least hardened. The statistical analysis of the results is carried out using the tables of A. Kramer (Food Technology, 17(12), 124–125, 1963).

Results

| Testers | 1 | 2 | 3 | 4 | 5 | 6 | 7 | 8 | 9 | 10 | Σ of the grades |
|---|---|---|---|---|---|---|---|---|---|---|---|
| Lock A | 1 | 1 | 1 | 1 | 1 | 1 | 1 | 1 | 1 | 1 | 10 |
| Lock B | 2 | 2 | 2 | 2 | 2 | 2 | 2 | 2 | 2 | 2 | 20 |

Conclusion

The locks treated with the composition A according to the invention comprising the alkylamido ether carboxylic surfactant are significantly harder (at the 5 level) than those treated with the composition comprising the surfactant of the prior art.

EXAMPLE 3

The following shampoo composition was prepared:

| | |
|---|---|
| Sodium salt of formula: $CH_3(CH_2)_{10}-\overset{O}{\overset{\|}{C}}-NH-(CH_2CH_2O)_{\overline{n}}-CH_2COONa$ in which n has a mean value of 3 (Akypofoam 30 BV from Chem Y) | 14 g AM |
| ($C_9$–$C_{11}$)Alkyl polyglucoside-(1,4) as an aqueous solution comprising 40% of AM (Kag 40 from Kao) | 3 g AM |
| Poly(acrylic acid) as an aqueous solution comprising 25% of AM (Versicol E 5 from Allied Colloid) | 1 g AM |
| Diallyldimethylammonium chloride homopolymer as an aqueous solution comprising 40% of AM (Merquat 100 from Calgon) | 1.43 g AM |
| NaOH q.s. | pH 8 |
| NaCl | 2 g |
| Fragrance, preservative | q.s. |
| Demineralized water q.s. for | 100 g |

Hair washed with this shampoo exhibits good styling properties. Furthermore, the foaming power of such a composition is good.

What is claimed is:

1. A cosmetic or dermatological composition for the treatment of a keratinous substance, comprising, in a cosmetically or dermatologically acceptable medium, at least one amido ether carboxylic acid surfactant or a salt thereof, and at least one combination of at least one noncrosslinked anionic polymer and of at least one cationic polymer;

wherein said at least one amido ether carboxylic acid surfactant has the structure of formula (I):

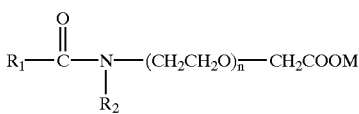

(I)

in which
R₁ is chosen from linear and branched, alkyl and alkenyl radicals having from 5 to 23 carbon atoms, and phenyl radicals substituted by an alkyl radical having from 6 to 10 carbon atoms;

R₂ is chosen from a hydrogen atom, alkyl radicals having from 1 to 3 carbon atoms, —(CH₂CH₂O)ₙCH₂COOM radicals, and —(CH₂CH₂O)ₘ radicals;

n and m, which are identical or different, are numbers from 1 to 20; and

M is chosen from hydrogen atom, alkali metals, NH₄⁺, and ammonium ions comprising a residue chosen from basic amino acids and aminoalcohols.

2. A process according to claim 1, wherein
R₁ is chosen from linear and branched alkyl radicals having from 8 to 18 carbon atoms;
R₂ is a hydrogen atom; and
n is a number from 1 to 10.

3. The composition according to claim 2, wherein R₁ is chosen from linear and branched alkyl radicals having from 10 to 16 carbon atoms; and
n is a number from 1 to 5.

4. The composition according to claim 1, wherein said at least one noncrosslinked anionic polymer is chosen from:
polymers comprising carboxyl units polymerized from unsaturated mono- or dicarboxylic acid monomers having the structure of formula (II):

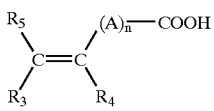

(II)

in which
n is an integer from 0 to 10,
A is a methylene group which is bonded to the carbon atom of the unsaturated group or to a neighboring methylene group when n is greater than 1 either directly or via a heteroatom,
R₃ is chosen from a hydrogen atom, a lower alkyl group, and a carboxyl group,
R₄ is chosen from a hydrogen atom, a lower alkyl group, a —CH₂—COOH group, a phenyl group, and a benzyl group, and
R₅ is chosen from a hydrogen atom, a phenyl group, and a benzyl group; and
polymers polymerized from monomers that contain sulphonic acid.

5. The composition according to claim 4, wherein said heteroatom is chosen from oxygen and sulphur.

6. The composition according to claim 4, wherein said monomers that contain sulphonic acid are chosen from vinylsulphonic, styrenesulphonic and acrylamidoalkylsulphonic monomers.

7. The composition according to claim 1, wherein said at least one noncrosslinked anionic polymer is chosen from:

A) homopolymers and copolymers of acrylic acid, methacrylic acid, and their salts, copolymers of acrylic acid and of acrylamide and their salts, and sodium salts of polyhydroxycarboxylic acids;

B)
(i) copolymers of acrylic acid or methacrylic acid with a monoethylenic monomer, said monoethylenic monomer being in free form or grafted onto a polyalkylene glycol, wherein said copolymers comprise, in their chain, one or more acrylamide units which are not N-substituted or are N-alkylated, N-hydroxyalkylated or a mixture of N-alkylated and N-hydroxyalkylated;
(ii) copolymers of acrylic acid and of C₁–C₄ alkyl methacrylate; and
(iii) terpolymers of vinylpyrrolidone, of acrylic acid and of C₁–C₂₀ alkyl methacrylate;

C) copolymers of crotonic acid, wherein said copolymers are not grafted or are grafted;

D)
(i) copolymers of monomers that contain maleic, fumaric or itaconic acids or anhydrides with vinyl esters, vinyl ethers, vinyl halides, phenylvinyl compounds, or acrylic acid and its esters;
(ii) copolymers of maleic, citraconic or itaconic anhydrides and of an allyl ester or methallyl ester,
wherein said copolymers comprise no other monomers or additionally comprise
one or more of an acrylamide group, methacrylamide group, α-olefin, acrylic ester, methacrylic ester, acrylic acid, methacrylic acid, and vinylpyrrolidone in their chain,
wherein said anhydrides are monoesterified or monoamidated; and E) polyacrylamides comprising carboxylate groups.

8. The composition according to claim 7, wherein said monoethylenic monomer is chosen from ethylene, styrene, vinyl esters, esters of acrylic acid, and esters of methacrylic acid.

9. The composition according to claim 7, wherein said polyalkylene glycol is polyethylene glycol.

10. The composition according to claim 7, wherein said copolymers of crotonic acid comprise, in their chain, vinyl acetate units, vinyl propionate units, or a mixture thereof.

11. The composition according to claim 7, wherein said copolymers of crotonic acid comprise one or more allyl esters, methallyl esters, vinyl ethers of linear and branched saturated carboxylic acids comprising long hydrocarbon chains, and vinyl esters of linear and branched saturated carboxylic acids comprising long hydrocarbon chains.

12. The composition according to claim 11, wherein said long hydrocarbon chains contain at least 5 carbon atoms.

13. The composition according to claim 1, wherein said at least one noncrosslinked anionic polymer is chosen from:
acrylic acid homopolymers and methacrylic acid homopolymers;
acrylic acid copolymers,
copolymers of crotonic acid,
polymers of monomers that contain maleic, fumaric or itaconic acids or anhydrides with vinyl esters, vinyl ethers, vinyl halides, phenylvinyl compounds, or acrylic acid and its esters,
copolymers of methacrylic acid and of methyl methacrylate;
copolymers of methacrylic acid and of ethyl acrylate;

vinylpyrrolidone/acrylic acid/lauryl methacrylate terpolymers;

vinyl acetate/crotonic acid copolymers; and vinyl acetate/crotonic acid/polyethylene glycol terpolymers.

14. The composition according to claim 13, wherein said at least one noncrosslinked anionic polymer is chosen from: acrylic acid/ethyl acrylate/N-tert-butylacrylamide terpolymers; vinyl acetate/vinyl tert-butylbenzoate/crotonic acid terpolymers; crotonic acid/vinyl acetate/vinyl neododecanoate terpolymers; and monoesterified methyl vinyl ether/maleic anhydride copolymers.

15. The composition according to claim 1, wherein said at least one noncrosslinked anionic polymer is chosen from anionic grafted silicone polymers comprising a polysiloxane portion and a portion composed of a non-silicone organic chain, one of the two portions constituting the main chain of the polymer and the other being grafted onto the main chain.

16. The composition according to claim 15, wherein said anionic grafted silicone polymers are chosen from silicone polymers comprising a unit having the structure of formula (III):

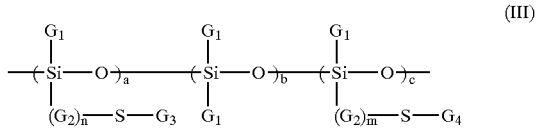

(III)

in which the $G_1$ radicals, which are identical or different, are chosen from hydrogen, $C_1$–$C_{10}$ alkyl radicals, and phenyl radicals;

the $G_2$ radicals, which are identical or different, are chosen from $C_1$–$C_{10}$ alkylene groups;

$G_3$ is chosen from polymeric residues resulting from the polymerization or homopolymerization of at least one anionic monomer possessing ethylenic unsaturation;

$G_4$ is chosen from polymeric residues resulting from the polymerization or homopolymerization of at least one hydrophobic monomer possessing ethylenic unsaturation;

m and n are identical or different, and are equal to 0 or 1;

a is an integer ranging from 0 to 50;

b is an integer ranging from 10 to 350; and c is an integer ranging from 0 to 50;

with the proviso that one of the parameters a and c is other than 0.

17. The composition according to claim 16, wherein said unit having the structure of formula (III) exhibits at least one of the following characteristics:

the $G_1$ radicals are chosen from $C_1$–$C_{10}$ alkyl radicals;

n is nonzero and the $G_2$ radicals are chosen from divalent $C_1$–$C_3$ radicals;

$G_3$ is chosen from polymeric radicals resulting from the polymerization or homopolymerization of at least one monomer of a carboxylic acid possessing ethylenic unsaturation; and $G_4$ is chosen from polymeric radicals resulting from the polymerization or homopolymerization of at least one monomer of $C_1$–$C_{10}$ alkyl acrylate or $C_1$–$C_{10}$ alkyl methacrylate.

18. The composition according to claim 16, wherein said unit having the structure of formula (III) simultaneously exhibits the following characteristics:

the $G_1$ radicals are methyl radicals;

n is nonzero and the $G_2$ radicals are propylene radicals;

$G_3$ is chosen from polymeric radicals resulting from the polymerization or homopolymerization of at least one or more of acrylic acid, methacrylic acid, or a mixture thereof;

$G_4$ is chosen from polymeric radicals resulting from the polymerization or homopolymerization of at least one or more of isobutyl acrylate, isobutyl methacrylate, methyl acrylate, methyl methacrylate, or a mixture of any two or more thereof.

19. The composition according to claim 16, wherein said unit having the structure of formula (III) exhibits at least one of the following characteristics:

the $G_1$ radicals are chosen from $C_1$–$C_{10}$ alkyl radicals;

n is nonzero and the $G_2$ radicals are chosen from divalent $C_1$–$C_3$ radicals;

$G_3$ is chosen from polymeric radicals resulting from the polymerization or homopolymerization of at least one monomer of a carboxylic acid possessing ethylenic unsaturation;

c is equal to 0.

20. The composition according to claim 1, wherein said at least one cationic polymer is chosen from quaternary cellulose ether polymers, copolymers of cellulose with a water-soluble quaternary ammonium monomer, cyclopolymers, cationic polysaccharides, silicone cationic polymers, quaternized or unquaternized vinylpyrrolidone/dialkylaminoalkyl acrylate copolymers, quaternized or unquaternized vinylpyrrolidone/dialkylaminoalkyl methacrylate copolymers, quaternary polymers of vinylpyrrolidone, quaternary polymers of vinylimidazole, polyaminoamides, and mixtures of any two or more thereof.

21. The composition according to claim 1, wherein said at least one amido ether carboxylic acid is present in an amount ranging from 0.1 to 30% by weight with respect to the total weight of the composition.

22. The composition according to claim 21, wherein said at least one amido ether carboxylic acid is present in an amount ranging from 0.5 to 20% by weight with respect to the total weight of the composition.

23. The composition according to claim 22, wherein said at least one amido ether carboxylic acid is present in an amount ranging from 1 to 15% by weight with respect to the total weight of the composition.

24. The composition according to claim 1, wherein said at least one cationic polymer is present in an amount ranging from 0.01% to 20% by weight with respect to the total weight of the composition.

25. The composition according to claim 14, wherein said at least one cationic polymer is present in an amount ranging from 0.1% to 15% by weight with respect to the total weight of the composition.

26. The composition according to claim 25, wherein said at least one cationic polymer is present in an amount ranging from 0.5% to 5% by weight with respect to the total weight of the composition.

27. The composition according to claim 1, wherein said at least one noncrosslinked anionic polymer is present in an amount ranging from 0.01 to 20% by weight of the total weight of the composition.

28. The composition according to claim 27, wherein said at least one noncrosslinked anionic polymer is present in an amount ranging from 0.05 to 15% by weight of the total weight of the composition.

29. The composition according to claim 28, wherein said at least one noncrosslinked anionic polymer is present in an amount ranging from 0.1 to 7% by weight of the total weight of the composition.

30. The composition according to claim 1, further comprising at least one additive chosen from sequestering agents, softeners, foam-modifying agents, colorants, pearlescent agents, moisturizing agents, antidandruff agents, antiseborrhoeic agents, suspending agents, ceramides, pseudoceramides, fatty acids with linear and branched $C_{16}$–$C_{40}$ chains, hydroxy acids, electrolytes, thickeners, fatty acid esters, esters of fatty acids, esters of glycerol, silicones, surfactants, fragrances, preservatives, sunscreen agents, proteins, vitamins, nonionic polymers, vegetable oils, animal oils, mineral oils, and synthetic oils.

31. The composition according to claim 1, wherein said cosmetically or dermatologically acceptable medium comprises water or a mixture of water and at least one cosmetically or dermatologically acceptable solvent.

32. The composition according to claim 1, wherein said keratinous substance is hair.

33. The composition according to claim 1, wherein said composition is in the form of a gel, milk, cream, lotion, or foam.

34. The composition according to claim 33, wherein said lotion is a thickened lotion.

35. The composition according to claim 1, wherein said composition is a shampoo.

36. The composition according to claim 1, wherein said composition is a rinse-out or leave-in product to be applied to hair, wherein said product is applied before or after shampooing, dyeing, bleaching, permanent waving, or a hair straightening process.

37. A cosmetic or dermatological composition for the treatment of a keratinous substance, comprising, in a cosmetically or dermatologically acceptable medium,
a sodium salt of formula:

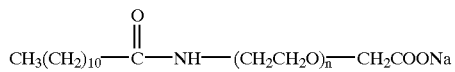

in which n has a mean value of 3;
a grafted silicone polymer with the structure:

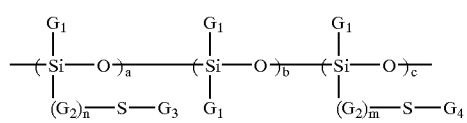

(III)

in which
$G_1$ radicals are methyl;
$G_2$ radicals are propyl;
$G_3$ is poly(methacrylic acid);
m is 0;
n is 1;
a is an integer ranging from 1 to 50;
b is an integer ranging from 10 to 350; and
c is 0; and
a polycondensate of adipic acid and of dietheylenetriamine crosslinked with epichlorohydrin.

38. A cosmetic or dermatological composition for the treatment of a keratinous substance, comprising, in a cosmetically or dermatologically acceptable medium, a sodium salt of the formula:

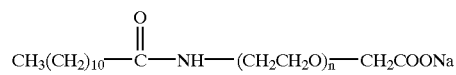

in which n has a mean value of 3;
poly(acrylic acid); and
a polycondensate of adipic acid and of diethylenetriamine crosslinked with epichlorohydrin.

39. A cosmetic or dermatological composition for the treatment of a keratinous substance, comprising, in a cosmetically or dermatologically acceptable medium,
a sodium salt of the formula:

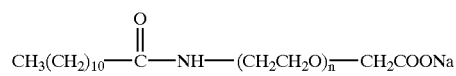

in which n has a mean value of 3;
poly(acrylic acid); and
diallyidimethylammonium chloride homopolymer.

40. A process for the cosmetic treatment of a keratinous substance, comprising
applying to said keratinous substance a cosmetic or dermatological composition comprising, in a cosmetically or dermatologically acceptable medium,
at least one amido ether carboxylic acid surfactant or a salt thereof, and
at least one combination of at least one noncrosslinked anionic polymer and of at least one cationic polymer;
wherein said at least one amido ether carboxylic acid surfactant has the structure of formula (I):

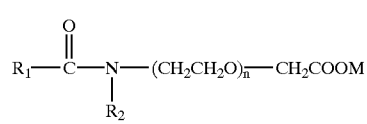

(I)

in which
$R_1$ is chosen from linear and branched, alkyl and alkenyl radicals having from 5 to 23 carbon atoms, and phenyl radicals substituted by an alkyl radical having from 6 to 10 carbon atoms;
$R_2$ is chosen from a hydrogen atom, alkyl radicals having from 1 to 3 carbon atoms, —$(CH_2CH_2O)_nCH_2COOM$ radicals, and —$(CH_2CH_2O)_m$ radicals; n and m, which are identical or different, are numbers from 1 to 20; and
M is chosen from hydrogen atom, alkali metals, $NH_4^+$, and ammonium ions comprising a residue chosen from basic amino acids and aminoalcohols.

41. The process according to claim 40, further comprising: rinsing said keratinous substance with water.

* * * * *